United States Patent
Choi

(10) Patent No.: US 7,771,759 B2
(45) Date of Patent: Aug. 10, 2010

(54) NATURAL ORIENTAL MEDICINAL COMPOSITION FOR THE PROMOTION OF HAIR GROWTH AND METHOD OF PREPARING THE SAME

(76) Inventor: Hyeong Geun Choi, 1873-32 Yeonsan-dong, Yeonjae-gu, Pusan 611-834 (KR)

( * ) Notice: Subject to any disclaimer, the term of this patent is extended or adjusted under 35 U.S.C. 154(b) by 500 days.

(21) Appl. No.: 11/689,349

(22) Filed: Mar. 21, 2007

(65) Prior Publication Data

US 2007/0269532 A1    Nov. 22, 2007

(30) Foreign Application Priority Data

Mar. 21, 2006    (KR) .................. 10-2006-0025863
Oct. 18, 2006    (KR) .................. 10-2006-0101408

(51) Int. Cl.
- A61K 36/48     (2006.01)
- A61K 36/13     (2006.01)
- A61K 36/68     (2006.01)
- A61K 36/254    (2006.01)
- A61K 36/752    (2006.01)
- A61K 36/8962   (2006.01)

(52) U.S. Cl. ............... 424/757; 424/770; 424/773; 424/736; 424/752; 424/754; 424/728; 424/738; 424/750; 424/195.15; 424/777

(58) Field of Classification Search ............ None
See application file for complete search history.

(56) References Cited

U.S. PATENT DOCUMENTS

| 6,254,858 B1 * | 7/2001 | Shim ................. 424/70.1 |
| 6,861,077 B1 * | 3/2005 | Cannell et al. ......... 424/725 |
| 2003/0113287 A1 * | 6/2003 | Park ................. 424/74 |

FOREIGN PATENT DOCUMENTS

| CN | 1448155 A | * | 10/2003 |
| DE | 3912637 A | * | 1/1991 |
| JP | 59190911 A | * | 10/1984 |
| JP | 03206019 A | * | 9/1991 |
| JP | 03227911 A | * | 10/1991 |
| JP | 06145028 A | * | 5/1994 |
| KR | 2002096780 A | * | 12/2002 |
| KR | 2003016150 A | * | 2/2003 |
| RU | 2014826 C1 | * | 6/1994 |

* cited by examiner

*Primary Examiner*—Christopher R. Tate
*Assistant Examiner*—Deborah A. Davis
(74) *Attorney, Agent, or Firm*—LRK Patent Law Firm

(57) ABSTRACT

Disclosed herein is a natural oriental medicinal composition for the promotion of hair growth. The oriental medicinal composition comprises a black bean extract, a tangerine extract, a potato extract, a pine needle extract and a quartzite powder.

Since the oriental medicinal composition comprises crude drugs extracted from natural substances that can prevent hair loss, it is effective for hair growth and has ensured biostability. Particularly, the oriental medicinal composition allows newborn hair to grow in the form of stiff hair.

4 Claims, No Drawings

NATURAL ORIENTAL MEDICINAL COMPOSITION FOR THE PROMOTION OF HAIR GROWTH AND METHOD OF PREPARING THE SAME

INCORPORATION BY REFERENCE

This application claims priority to Korean Patent Application Serial No. 10-2006-0025863 filed on Mar. 21, 2006, and Korean Patent Application Serial No. 10-2006-0101408 filed on Oct. 18, 2006.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a natural oriental medicinal composition for the promotion of hair growth, and more specifically to a natural oriental medicinal composition for the promotion of hair growth which comprises extracts and powders from particular kinds of plants and minerals.

BACKGROUND OF THE INVENTION

Numerous hypotheses have been proposed regarding causes of alopecia and hair loss. These hypotheses include, for example, dysfunction of male hormones secreted from hair roots and organs (e.g., sebaceous glands), reduction in the amount of blood flowing into hair follicles, excessive sebum secretion, formation of peroxides, abnormality of the state of the scalp due to the proliferation of bacteria, hereditary factors, and aging. However, despite the gradual increase in the number of people who suffer from hair loss and the decrease in the age of alopecia patients, the precise mechanism of hair loss still remains unknown.

Normally, humans have more than 1.3 million hairs in the body and more than 100,000 hairs on the head. Each hair undergoes different stages of a growth cycle consisting of anagen, catagen and telogen phases. "Hair loss" refers to the state in which, due to certain causes, the number of hairs is zero or significantly low when compared to the normal state. Hair loss can be categorized into telogen effluvium and anagen effluvium; the former is a general phenomenon wherein hairs fall off in the telogen phase, while the latter is an abnormal hair loss phenomenon generally referred to as alopecia. Alopecia relates to a state in which the telogen phase is relatively long and the anagen phase is relatively short. When the telogen phase is lengthened, the revitalization of hair is difficult.

No effective treatment for alopecia is known. Traditional treatments include the use of proper tools (e.g., brushes) to apply physical stimuli to the head, or therapeutic compounds to remove or attenuate the above-mentioned causes of alopecia. For instance, based on the hypothesis that hormones are associated with the treatment of alopecia, preparations comprising female hormones as active ingredients have been developed. However, these hormone preparations were reported to be ineffective for alopecia and to cause skin inflammation and other side effects due to the administration of hormones. The use of the hormone preparations is currently not allowed.

In recent years, minoxidil, which is commercially available from Upjohn Company, U.S.A. and preparations (Crinos, Co., Italy) comprising trichosaccharide as an active ingredient have been introduced into the market. However, these preparations have shown no distinct effect on hair loss and caused side effects in terms of the stability in the human body.

Most hair restorers developed hitherto use chemical substances and temporarily promote the circulation of blood to expand capillary vessels, thus stimulating hair roots. Accordingly, conventional hair restorers provide temporary relief for hair loss and are only effective for hair loss induced by excessively secreted sebum.

In addition, various methods have been developed to prevent or treat hair loss by revitalizing hair follicles or controlling the mechanism of antioxidants. The revitalization of hair follicles is achieved by activating hair follicles by immune enhancement to supply saccharides as nutrients to the hair follicles. According to these methods, however, newborn hair does not have an original form, but is temporarily formed by cell division and stimuli, resulting in shortened life of the hair.

Considering that over $3.5 billion is spent in the United States alone on treatments of hair loss, research on developing a solution to the aforementioned problems continues. Although many hair restorers have been proposed to prevent and treat hair loss, no hair restorer has yet to succeed in overcoming these problems.

Citation or identification of any document in this application is not an admission that such document is available as prior art to the present invention.

SUMMARY OF THE INVENTION

The present invention was developed in view of the problems of the prior art. It is an objective of the present invention to provide a natural oriental medicinal composition for the promotion of hair growth which comprises crude drugs extracted from natural substances. These substances can prevent hair loss, are effective for hair growth and have ensured biostability. It is a further objective of the present invention to provide a method for preparing the oriental medicinal composition.

To solve the problems of the prior art, the present inventors have earnestly and intensively conducted research using an oriental medical approach to develop a natural oriental medicinal composition for the promotion of hair growth using natural substances that are biologically safe, can prevent hair loss, and can enhance hair growth. In addition, the present inventors have conducted research to develop a technique for strengthening hair at the initial stage of hair formation to extend the anagen phase so that the life of hair is prolonged.

As a result, the present inventors have found that when a composition comprising quartzite was applied, newborn hair grows in the form of stiff hair. The present invention has been achieved based on this finding.

Therefore, it is a primary objective of the present invention to provide a natural oriental medicinal composition for the promotion of hair growth which comprises quartzite, and to provide a method for preparing this oriental medicinal composition.

That is, it is one objective of the present invention to provide a natural oriental medicinal composition for the promotion of hair growth which uses purified oriental medicinal materials and grains to remove fats excessively secreted in response to invasion of pathogenic wind, thereby inhibiting the activity of harmful bacteria; to sufficiently enhance the circulation of blood, thereby ensuring the supply of nutrients to hair roots and activating the formation of cells; and to provide a method for preparing this oriental medicinal composition.

It is another objective of the present invention to provide a natural oriental medicinal composition for the promotion of hair growth that is suitable for the treatment of hair loss caused by the lack of nutrients, which is observed when the flow of vital energy is weakened. In this objective, vitamins, a high level of proteins (i.e. amino acids), and hematopoietic elements that are indispensable for the revitalization of hair, are supplied to enhance the flow of vital energy. Further, an objective is to provide a method for preparing this oriental medicinal composition.

It is another object of the present invention to provide a natural oriental medicinal composition for the promotion of hair growth that allows newborn hair to grow in an original form through the control of hormone secretion, prevents hair loss, improves the elasticity of existing hair, and strengthens revitalized hair roots; it is also an objective to provide a method for preparing this oriental medicinal composition.

It is yet another object of the present invention to provide a natural oriental medicinal composition for the promotion of hair growth that prevents hair loss induced due to specific physical constitution and hereditary factors, and that effectively revitalizes the hair of patients suffering from alopecia areata due to scalp inflammation, stress, and other various diseases. The prevention of hair loss is based on an oriental medical principle of hair revitalization; that is, a hair revitalization mechanism due to improvement of blood circulation, enhancement of hair roots, control of hormones, activation of cells, and high levels of nutrients. It is an objective to provide a method for preparing this oriental medicinal composition.

In accordance with one aspect of the present invention for achieving the above objectives, there is provided a natural oriental medicinal composition for the promotion of hair growth (hereinafter, referred to simply as an "oriental medicinal composition") which may comprise a black bean extract, a tangerine extract, a potato extract, a pine needle extract and a quartzite powder.

Thus, the oriental medicinal composition of the present invention may comprise about 100 parts by weight of the quartzite, about 20 to about 200 parts by weight of the black bean extract, about 20 to about 200 parts by weight of the tangerine extract, about 20 to about 200 parts by weight of the potato extract, and about 20 to about 200 parts by weight of the pine needle extract.

The oriental medicinal composition of the present invention may also comprise an onion extract, a ginkgo nut extract, a *Fructus schizandrae* (the dried ripe fruit of *Schisandra chinensis*) extract, a *Fructus lycii* (the dried ripe fruit of *Lycium barbarum*) extract, an oyster mushroom (*Pleurotus ostreatus*) extract, and/or a barley extract.

Therefore, the oriental medicinal composition of the present invention may also comprise about 50 to about 250 parts by weight of the onion extract, about 30 to about 200 parts by weight of the ginkgo nut extract, about 30 to about 200 parts by weight of the *Fructus schizandrae* extract, about 50 to about 250 parts by weight of the *Fructus lycii* extract, about 30 to about 200 parts by weight of the oyster mushroom extract, and/or about 20 to about 200 parts by weight of the barley extract, based on about 100 parts by weight of the quartzite.

The oriental medicinal composition of the present invention may further comprise a taro extract, a *Fructus rubi* (the dried fruit of *Rubus chingii*) extract, a jade powder, a wild ginseng extract, and/or a loess powder.

As such, the oriental medicinal composition of the present invention may further comprise about 10 to about 150 parts by weight of the taro extract, about 50 to about 250 parts by weight of the *Fructus rubi* extract, about 50 to about 250 parts by weight of the jade powder, about 50 to about 250 parts by weight of the wild ginseng extract, and/or about 50 to about 250 parts by weight of the loess powder, based on about 100 parts by weight of the quartzite.

The oriental medicinal composition of the present invention may further comprise about 1 to about 10 parts by weight of a gold powder, based on about 100 parts by weight of the quartzite.

In accordance with another aspect of the present invention, there is provided a method for preparing an oriental medicinal composition, wherein the method can comprise the steps of preparing crude drugs, mixing the crude drugs, and reconcentrating the mixture by heating.

The step of preparing crude drugs can comprise the substeps of: heating selected plants at about 90 to about 130° C. for about 8 to about 15 hours and filtering the heated plants to obtain respective extracts from the plants; heating the extracts at about 50 to about 80° C. for about 12 to about 48 hours to obtain respective concentrates; and drying the concentrates and pulverizing to obtain respective powders.

The reconcentration step can be performed by mixing about 50 to about 250 parts by weight of the mixture of the crude drugs with about 100 parts by weight of water and heating the resulting mixture at about 80 to about 140° C. for about 12 to about 48 hours.

The crude drugs can be obtained from black beans, tangerines, potatoes, pine needles and quartzite.

Alternatively, the crude drugs can also be obtained from black beans, tangerines, potatoes, pine needles, quartzite, onions, ginkgo nuts, *Fructus schizandrae, Fructus lycii*, oyster mushrooms and barley.

Further, the crude drugs can be obtained from black beans, tangerines, potatoes, pine needles, quartzite, onions, ginkgo nuts, *Fructus schizandrae, Fructus lycii*, oyster mushrooms, barley, taro, *Fructus rubi*, jade, wild ginseng and loess.

The term "crude drug" as used herein refers to an ingredient that is beneficial to humans. The crude drug can be prepared from a naturally occurring material either without any processing or through processing such as drying, cutting, heating, extracting or pulverizing. Depending on the origin (e.g., a plant, mineral or animal) of the naturally occurring material, the crude drug can be classified into a plant, mineral or animal crude drug. In this context, crude drug can also refer to the plant extracts or mineral powder discussed in the present invention.

The term "oriental" as used herein describes Eastern principles or philosophies as applied to medicine. The term can also be used to indicate "organic" or "natural" or "homeopathic" or to relate to nutrition. Thus, the oriental composition of the present invention can be an organic composition or a natural composition or a homeopathic composition. It is also contemplated that the term "oriental" indicates that the components of the composition are readily available in nature.

Finally, it is an objective of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION

The present invention provides a method for preparing an oriental medicinal composition, the method comprising the steps of preparing crude drugs, mixing the crude drugs, and reconcentrating the mixture by heating.

The oriental medicinal composition of the present invention is achieved based on an oriental medical principle of hair revitalization, that is, improvement of blood circulation, enhancement of hair roots, control of hormones, activation of cells, and high levels of nutrients. Taking into consideration the circulation of blood by the action of light energy, the enzymatic metabolism of carbohydrates, the ability to form cells and the ability to inhibit the formation of active oxygen, it is preferred that the crude drugs contain ingredients capable of supplying vitamins, amino acids, and hematopoietic elements essential for the revitalization of hair, and that can improve the flow of blood by the action of light energy.

The crude drugs are preferably a black bean extract, a tangerine extract, a potato extract, a pine needle extract, and quartzite.

The crude drugs are more preferably a black bean extract, a tangerine extract, a potato extract, a pine needle extract, and quartzite, and further an onion extract, a ginkgo nut extract, a *Fructus schizandrae* extract, a *Fructus lycii* extract, an oyster mushroom extract, and/or a barley extract. The crude drugs are even more preferably a black bean extract, a tangerine extract, a potato extract, a pine needle extract, quartzite, an onion extract, a ginkgo nut extract, a *Fructus schizandrae* extract, a *Fructus lycii* extract, an oyster mushroom extract, and a barley extract, and further a taro extract, a *Fructus rubi* extract, a jade powder, a wild ginseng extract, and/or loess. The crude drugs can also include gold powder.

The crude drugs effectively induce the promotion of hair growth. The step of preparing the crude drugs includes the sub-steps of: heating the selected plants at about 90 to about 130° C. for about 8 to about 15 hours and filtering the heated plants to obtain extracts from the plants; heating the extracts at about 50 to about 80° C. for about 12 to about 48 hours to obtain concentrates; and drying the concentrates and pulverizing to obtain respective nanometer-sized powders. The nanometer-sized powders of the respective crude drugs are highly soluble without any precipitation in the subsequent mixing and reconcentration steps.

The oriental medicinal composition of the present invention preferably comprises about 100 parts by weight of the quartzite, about 20 to about 200 parts by weight of the black bean extract, about 20 to about 200 parts by weight of the tangerine extract, about 20 to about 200 parts by weight of the potato extract, and about 20 to about 200 parts by weight of the pine needle extract. More preferably, the oriental medicinal composition of the present invention further comprises about 50 to about 250 parts by weight of the onion extract, about 30 to about 200 parts by weight of the ginkgo nut extract, about 30 to about 200 parts by weight of the *Fructus schizandrae* extract, about 50 to about 250 parts by weight of the *Fructus lycii* extract, about 30 to about 200 parts by weight of the oyster mushroom extract, and/or about 20 to about 200 parts by weight of the barley extract, based on about 100 parts by weight of the quartzite. Even more preferably, the oriental medicinal composition of the present invention further comprises about 10 to about 150 parts by weight of the taro extract, about 50 to about 250 parts by weight of the *Fructus rubi* extract, about 50 to about 250 parts by weight of the jade powder, about 50 to about 250 parts by weight of the wild ginseng extract, and/or about 50 to about 250 parts by weight of the loess, based on about 100 parts by weight of the quartzite. Finally, the oriental medicinal composition can further be comprised of about 1 to about 10 parts by weight of a gold powder, based on about 100 parts by weight of the quartzite.

The contents of the respective crude drugs were determined through repeated experiments while taking into consideration the optimum effects, e.g., a hair tonic comprising the oriental medicinal composition of the present invention is used to allow newborn hair to have the same thickness as the original hair (stiff hair) of the user, and from the viewpoint of economic efficiency, i.e. minimized production costs. If the crude drugs are mixed in amounts of less than the respective contents defined above, the thickness of the revitalized hair is as small as that of fluff and the number of hairs lost decreases.

The reconcentration step is performed by mixing about 50 to about 250 parts by weight of the mixture of the crude drugs with about 100 parts by weight of water, and heating the resulting mixture at about 80 to about 140° C. for about 12 to about 48 hours.

The respective crude materials used to prepare the oriental medicinal composition of the present invention are well known in the art. Particularly, onions, black beans, oyster mushrooms, barley, ginkgo nuts, *Fructus schizandrae*, potatoes, *Fructus lycii*, wild ginseng, taro, pine needles, tangerines and *Fructus rubi* are commercially available as natural foods. These crude materials can be purchased as general products, are preferably organic products, and are more preferably products cultivated in Korea without using any agricultural chemical. Then, the selected crude materials are washed. Hereinafter, the efficacy of the crude drugs will be explained below.

The onion extract used in the oriental medicinal composition of the present invention serves as a source of trisulfide. The vitamins and inorganic calcium phosphate contained in the onion extract remove harmful substances in the blood and promote the absorption of vitamin B 1, a hormone for hair formation. This activates metabolism, thereby preventing the formation of blood clots. In addition, the onion extract exerts synergistic effects with the black bean extract.

The black bean extract serves as a source of tocopherol, plant estrogen, and saponin. The black bean extract contains substances essential for hair growth, such as high-quality proteins, lipids, and vitamins B1 and B2. The black bean extract controls the metabolism of saccharides, which are energy sources for hair, and inhibits aging to prevent hair loss induced due to hereditary factors.

The oyster mushroom extract serves as a source of vitamin B2 and ergosterin. Vitamin B2 group contained in the oyster mushroom extract promotes the growth of hair and supplies substances necessary for the metabolism of saccharides. *Saccharides* are indispensable elements for the activation of hair follicle cells. In addition, the oyster mushroom extract prevents skin inflammation (dermatitis), exhibits antitumoral effects, and impedes the absorption of bad cholesterol so as to enhance the immune systems, thereby strengthening hair roots.

The barley extract exhibits antiphlogistic effects, is indispensable for the activation of hair follicle cells, and contains large amounts of vitamin B group, which is a main ingredient for the energy metabolism of carbohydrates.

The quartzite stimulates hair roots to improve the circulation of blood so that cells are sufficiently formed and revitalized. That is, the quartzite promotes the absorption of various crude drugs into the scalp by the action of light energy.

The ginkgo nut extract acts as a source of flavonoid, globulin and elgosterin, absorbs bad cholesterol to prevent the formation of extravasated blood, and exerts synergistic effects with grains to make the scalp clean.

The *Fructus schizandrae* extract acts to assist in the formation of amino acid transaminases (e.g., GOT and GPT) to supply proteins necessary for the revitalization of hair, thereby controlling secretion of hormones through stimulation of brain waves.

The potato extract is a source of collagen and contains collagen ingredients that revitalize cells and enhance the elasticity of hair roots through balanced humors, i.e. controlled hormone secretion.

The *Fructus lycii* extract acts to produce immune enhancing substances, exhibits hematopoietic action, and promotes the formation of growth hormones. Accordingly, the *Fructus lycii* extract has been used as a medicinal material effective for the prevention of hair loss.

The extract from wild ginseng, known as an herb of eternal youth, promotes the formation of cells and improves the bloodstream to sufficiently supply nutrients to hair roots.

The taro extract acts as a source of glucuronic acid, brings down fever, relieves inflammation, and activates the functions of the kidney and liver to prevent aging.

The pine needle extract acts as a source of terpene, α-pinene and β-pinene, and inhibits the formation of lipid peroxides from linoleic acid, palmitic acid and 5-oleic acid by the action of active oxygen to prevent aging. In addition, the pine needle extract contains essential amino acids, which cannot be synthesized within the body, to revitalize elastic hairs.

The tangerine extract acts as a source of ascorbic acid, recovers fatigue, promotes metabolism, lowers the level of cholesterol, and is effective for the prevention of arteriosclerosis.

The *Fructus rubi* extract is a source of polyphenols, tannin, saponin and anthocyanine, and stimulates the functions of the adrenal cortex to activate growth functions, thus rendering hair black.

The jade acts to discharge of wastes from the body and improves the bloodstream.

The loess is mixed with grains to remove excessively secreted sebum, thereby making the scalp clean.

Ions (low current) of the gold (24K) bind to ions present in blood to stimulate the leucocytes, thereby promoting the circulation of blood (effects of negatively charged ions). In addition, a photocurrent generated from the gold induces resonance of moisture contained in the body to promote the activation of the moisture so that the scalp is maintained in a fresh state.

Thus, the action of the light energy released from the quartzite promotes the absorption of trisulfide extracted from onion; vitamin C, vitamin B group, and vitamin E (tocopherol) extracted from black bean, oyster mushroom, and ginkgo nut; and polysaccharides (e.g., glucose, maltose and tannin) contained as nutrients in taro, potato and barley into the scalp. In addition, the quartzite promotes the bloodstream. Furthermore, terpene extracted from pine needles, ginkgo nut, *Fructus lycii, Fructus schizandrae,* and *Fructus rubi* functions to inhibit the formation of active oxygen, removes excessively secreted lipid peroxides due to its antibacterial activity, and inhibits the formation of lipid peroxides to assist the revitalization of hair.

Preferably, the oriental medicinal compositions are comprised of the plant extracts and mineral powders mixed with water. Alternatively, adjuvants normally used in the field of application considered, in particular in the cosmetic field, such as surfactants, thickening or gelling agents, cosmetic agents, preservatives, alkalinizing or acidifying agents well known in the state of the art, may be added. The nature and the quantity of these adjuvants would be well known to persons skilled in the art so as to obtain the form of presentation desired for the composition. Notably, a person skilled in the art would choose appropriate compounds/ingredients so that the advantageous properties of the composition according to the invention are not, or not substantially, impaired by the addition.

The oriental medicinal compositions according to the invention may be provided in the form of a lotion which is thickened to a greater or lesser degree, a gel, an emulsion or a cream, or in a liposomal form. They may be optionally used in pressurized form as an aerosol or as a spray from a pump dispenser. It is well known in the art the methods that can be applied in order to alter the oriental medicinal composition so that it is in the above-mentioned forms. Again, a person skilled in the art would choose additional ingredients that would not impair the advantageous properties of the composition according to the invention.

The invention will now be further described by way of the following non-limiting examples which further illustrate the invention, and are not intended, nor should they be interpreted to, limit the scope of the invention.

EXAMPLES

Example 1

Preparation of Oriental Medicinal Composition

Example 1-1

Black beans, tangerines, pine needles and quartzite were thoroughly washed with water, and potatoes were cut to a predetermined size.

Then, 3 g of the black beans were added to 50 ml of purified water heated at 120° C. for 11 hours using an alcohol lamp, and filtered to obtain black beans extract. The filtrate, that is the extract, was heated at 55° C. for 14 hours to obtain black beans concentrate. The concentrate was dried for 24 hours and pulverized to obtain a powder having a particle diameter not larger than 100 μm. The pine needles, the tangerines and the potatoes were processed in the same manner as in the processing of the black beans to obtain respective powders. Also, the quartzite was pulverized to obtain a powder having a particle diameter not larger than 100 μm.

Subsequently, 3 g of the black bean powder, 3 g of the pine needle powder, 3 g of the tangerine powder, and 3 g of the potato powder were added to 40 g of purified water, and mixed with 4 g of the quartzite powder. The resulting mixture was heated at 110° C. using an alcohol lamp for 24 hours to prepare an oriental medicinal composition.

Example 1-2

Black beans, tangerines, pine needles, quartzite, ginkgo nuts, *Fructus schizandrae, Fructus lycii*, oyster mushrooms, and barley were thoroughly washed. Onions and potatoes were cut to a predetermined size.

Predetermined amounts of the black beans, the onions, the oyster mushrooms, the ginkgo nuts, the *Fructus schizandrae*, the pine needles, the tangerines, the potatoes, the *Fructus lycii*, and the barley were processed in the same manner as in the processing of the black beans described in Example 1-1 to obtain respective powders.

Subsequently, 4 g of the onion powder, 3 g of the black bean powder, 3 g of the oyster mushroom powder, 3.5 g of the ginkgo nut powder, 3.5 g of the *Fructus schizandrae* powder, 3 g of the pine needle powder, 3 g of the tangerine powder, 3 g of the potato powder, 4 g of the *Fructus lycii* powder, and 3 g of the barley powder were added to 40 g of purified water, and mixed with 4 g of the quartzite powder having a particle diameter not larger than 100 µm. The resulting mixture was heated at 110° C. using an alcohol lamp for 24 hours to prepare an oriental medicinal composition.

Example 1-3

Black beans, tangerines, pine needles, quartzite, ginkgo nuts, *Fructus schizandrae, Fructus lycii*, oyster mushrooms, barley, taro, *Fructus rubi*, jade, wild ginseng, and loess were thoroughly washed. Onions and potatoes were cut to a predetermined size.

Predetermined amounts of the black beans, the onions, the oyster mushrooms, the taro, the ginkgo nuts, the *Fructus schizandrae*, the pine needles, the tangerines, the potatoes, the *Fructus lycii*, the barley, and *Fructus rubi* were processed in the same manner as in the processing of the black beans described in Example 1-1 to obtain respective powders. Also, the quartzite, the jade and the loess were processed in the same manner as in the processing of the quartzite described in Example 1-1 to obtain respective powders.

Subsequently, 4 g of the onion powder, 3 g of the black bean powder, 3.5 g of the oyster mushroom powder, 2.5 g of the taro powder, 3.5 g of the ginkgo nut powder, 3.5 g of the *Fructus schizandrae* powder, 3 g of pine needle powder, 3 g of the tangerine powder, 3 g of the potato powder, 4 g of the *Fructus lycii* powder, 4 g of the wild ginseng powder, 3 g of the barley powder, and 4 g of the *Fructus rubi* powder were added to 40 g of purified water, and mixed with 4 g of the loess powder, 4 g of the quartzite powder, and 4 g of the jade powder, all of which had a particle diameter not larger than 100 µm. The resulting mixture was heated at 110 C. using an alcohol lamp for 24 hours to prepare an oriental medicinal composition.

Example 1-4

Black beans, tangerines, pine needles, quartzite, ginkgo nuts, *Fructus schizandrae, Fructus lycii*, oyster mushrooms, barley, taro, *Fructus rubi*, a jade, wild ginseng, and loess were thoroughly washed with water, and onions and potatoes were cut to a predetermined size.

Then, 3 g of the black beans were added to 50 ml of purified water, heated at 120° C. for 11 hours using an alcohol lamp, and filtered to obtain black beans extract. The filtrate, that is the extract, was heated at 55° C. for 14 hours to obtain black beans concentrate. The concentrate was dried for 24 hours and pulverized to obtain a powder having a particle diameter not larger than 100 µm. The onions, the oyster mushrooms, the taro, the ginkgo nuts, the *Fructus schizandrae*, the pine needles, the tangerines, the potatoes, the *Fructus lycii*, the wild ginseng, the barley, and *Fructus rubi* were processed in the same manner as in the processing of the black beans to obtain respective powders.

Also, the quartzite was pulverized to obtain a powder having a particle diameter not larger than 100 µm. The jade, the loess, and gold (24K) were processed in the same manner as in the processing of the quartzite to obtain respective powders.

Subsequently, 4 g of the onion powder, 3 g of the black bean powder, 3.5 g of the oyster mushroom powder, 2.5 g of the taro powder, 3.5 g of the ginkgo nut powder, 3.5 g of the *Fructus schizandrae* powder, 3 g of the pine needle powder, 3 g of the tangerine powder, 3 g of the potato powder, 4 g of the *Fructus lycii* powder, 4 g of the wild ginseng powder, 3 g of the barley powder, and 4 g of the *Fructus rubi* powder were added to 40 g of purified water, and mixed with 4 g of the loess, 4 g of the quartzite, 4 g of jade, and 1.25 mg of gold (24K), all of which had a particle diameter not larger than 100 µm. The resulting mixture was heated at 110° C. using an alcohol lamp for 24 hours to prepare an oriental medicinal composition.

Example 2

Preparation of Oriental Medicinal Composition—Alternative Embodiment

Example 2-1

An oriental medicinal composition was prepared in the same manner as in Example 1-1, except that 4 g of the black bean powder, 3 g of the pine needle powder, 4 g of the tangerine powder, and 3 g of the potato powder were mixed with 5 g of the quartzite powder.

Example 2-2

An oriental medicinal composition was prepared in the same manner as in Example 1-2, except that 5 g of the onion powder, 4 g of the black bean powder, 3.5 g of the oyster mushroom powder, 3.5 g of the ginkgo nut powder, 4 g of the *Fructus schizandrae* powder, 3 g of the pine needle powder, 4 g of the tangerine powder, 3 g of the potato powder, 5 g of the *Fructus lycii* powder, and 3 g of the barley powder were mixed with 5 g of the quartzite powder.

Example 2-3

An oriental medicinal composition was prepared in the same manner as in Example 1-3, except that 5 g of the onion powder, 4 g of the black bean powder, 3.5 g of the oyster mushroom powder, 3 g of the taro powder, 3.5 g of the ginkgo nut powder, 4 g of the *Fructus schizandrae* powder, 3 g of the pine needle powder, 4 g of the tangerine powder, 3 g of the potato powder, 5 g of the *Fructus lycii* powder, 3 g of the wild ginseng powder, 3 g of the barley powder, and 4 g of the

*Fructus rubi* powder were mixed with 3 g of the loess powder, 5 g of the quartzite powder, and 4 g of the jade powder.

Example 2-4

An oriental medicinal composition was prepared in the same manner as in Example 1-4, except that 5 g of the onion powder, 4 g of the black bean powder, 3.5 g of the oyster mushroom powder, 3 g of the taro powder, 3.5 g of the gingko nut powder, 4 g of the *Fructus schizandrae* powder, 3 g of the pine needle powder, 4 g of the tangerine powder, 3 g of the potato powder, 5 g of the *Fructus lycii* powder, 3 g of the wild ginseng powder, 3 g of the barley powder, and 4 g of the *Fructus rubi* powder were mixed with 3 g of the loess powder, 5 g of the quartzite powder, 4 g of the jade powder, and 1.25 mg of the gold (24K) powder.

Example 3

Preparation of Oriental Medicinal Composition—Alternative Embodiment

Example 3-1

An oriental medicinal composition was prepared in the same manner as in Example 1-1, except that 2 g of the black bean powder, 2 g of the pine needle powder, 5 g of the tangerine powder, and 3 g of the potato powder were mixed with 5 g of the quartzite powder.

Example 3-2

An oriental medicinal composition was prepared in the same manner as in Example 1-2, except that 3 g of the onion powder, 2 g of the black bean powder, 3.5 g of the oyster mushroom powder, 3.5 g of the ginkgo nut powder, 4 g of the *Fructus schizandrae* powder, 2 g of the pine needle powder, 5 g of the tangerine powder, 3 g of the potato powder, 5 g of the *Fructus lycii* powder, and 3 g of the barley powder were mixed with 5 g of the quartzite powder.

Example 3-3

An oriental medicinal composition was prepared in the same manner as in Example 1-3, except that 3 g of the onion powder, 2 g of the black bean powder, 3.5 g of the oyster mushroom powder, 3 g of the taro powder, 3.5 g of the ginkgo nut powder, 4 g of the *Fructus schizandrae* powder, 2 g of the pine needle powder, 5 g of the tangerine powder, 3 g of the potato powder, 5 g of the *Fructus lycii* powder, 4 g of the wild ginseng powder, 3 g of the barley powder, and 5 g of the *Fructus rubi* powder were mixed with 4 g of the loess, 5 g of the quartzite, and 4 g of the jade.

Example 3-4

An oriental medicinal composition was prepared in the same manner as in Example 1-4, except that 3 g of the onion powder, 2 g of the black bean powder, 3.5 g of the oyster mushroom powder, 3 g of the taro powder, 3.5 g of the ginkgo nut powder, 4 g of the *Fructus schizandrae* powder, 2 g of the pine needle powder, 5 g of the tangerine powder, 3 g of the potato powder, 5 g of the *Fructus lycii* powder, 4 g of the wild ginseng powder, 3 g of the barley powder, and 5 g of the *Fructus rubi* powder were mixed with 4 g of the loess, 5 g of the quartzite, 4 g of the jade, and 1.25 mg of gold (24K).

Example 4

Clinical Tests of the Oriental Medicinal Compositions

Clinical tests of each of the oriental medicinal compositions of Examples 1, 2, and 3 were conducted on 100 men and women suffering from alopecia, and the test results are shown in Table 1. The oriental medicinal compositions were applied twice (each 5 ml) daily for six months around hair roots of the scalp where hair loss occurred. The state of the scalp was then observed.

TABLE 1

|  | Example 1-1 | Example 1-2 | Example 1-3 | Example 1-4 |
| --- | --- | --- | --- | --- |
| Excellent | 25 | 28 | 32 | 35 |
| Good | 14 | 16 | 18 | 20 |
| Decrease of hair loss | 11 | 12 | 14 | 15 |
| Ineffective | 25 | 19 | 11 | 5 |
| Not available | 25 | 25 | 25 | 25 |

|  | Example 2-1 | Example 2-2 | Example 2-3 | Example 2-4 |
| --- | --- | --- | --- | --- |
| Excellent | 13 | 14 | 16 | 18 |
| Good | 7 | 8 | 9 | 10 |
| Decrease of hair loss | 6 | 7 | 7 | 8 |
| Ineffective | 15 | 12 | 9 | 5 |
| Not available | 59 | 59 | 59 | 59 |

|  | Example 3-1 | Example 3-2 | Example 3-3 | Example 3-4 |
| --- | --- | --- | --- | --- |
| Excellent | 7 | 8 | 9 | 10 |
| Good | 4 | 4 | 5 | 5 |
| Decrease of hair loss | 5 | 6 | 7 | 8 |
| Ineffective | 15 | 13 | 10 | 8 |
| Not available | 69 | 69 | 69 | 69 |

The oriental medicinal composition was considered to be "excellent" when hair having the same thickness as the original hair of the users (i.e. newborn hair was stiff) was grown. When thin hair in the form of fluff was grown, the oriental medicinal composition was judged to be 'good'. If no newborn hair was grown and the number of hairs lost was decreased, the oriental medicinal composition was judged as "decrease of hair loss." When there is no difference in the density before and after the test, the oriental medicinal composition was regarded to be "ineffective." If no clinical test result was obtained from the users, the oriental medicinal composition was judged to be "not available." As can be seen from the data shown in Table 1, assuming that the oriental medicinal compositions of Example 1-4 and Example 3-4 have an efficiency of 100%, the oriental medicinal compositions of Example 1-1 and Example 3-1 have an efficiency of about 70%, the oriental medicinal compositions of Example 1-2 and Example 3-2 have an efficiency of about 80%, and the oriental medicinal compositions of Example 1-3 and Example 3-3 have an efficiency of about 90%.

Regarding the type of hair loss, the oriental medicinal composition of Example 1-4 was applied to 90 males and females suffering from hair loss due to hereditary factors, 70 males and females suffering from hair loss due to alopecia areata and a variety of diseases, and 40 males and females at the initial stage of hair loss. The clinical test results are shown in Table 2.

TABLE 2

| Type of hair loss | Hair growth cycle (day) | Number of patients |
| --- | --- | --- |
| Hair loss due to | 180 | 60 |
| hereditary factors | 140 | 20 |
| (90 patients) | 120 | 6 |
| | Not available | 4 |
| Hair loss due to alopecia areata | 120 | 30 |
| and a variety of diseases | 100 | 20 |
| (70 patients) | 80 | 10 |
| | Not available | 10 |
| Initial stage of hair loss | 60 | 15 |
| (40 patients) | 50 | 10 |
| | 40 | 5 |
| | Not available | 10 |

As can be seen from the data shown in Table 2, about 85% of the patients using the oriental medicinal compositions experienced excellent hair growth effects. Although there was a difference in the time when hair began to grow between the individuals, the oriental medicinal composition was effective in all patients suffering from various types of alopecia. Particularly, excellent hair growth effects were observed in the patients suffering from hair loss due to hereditary factors.

Based on these observations, the oriental medicinal compositions of the present invention promoted hair growth through the supply of optimal nutrients, the circulation of blood due to the action of light energy, the enzymatic metabolism of carbohydrates, the ability to form cells, and the ability to inhibit the formation of active oxygen, thereby resulting in prevention of hair loss and revitalization of hair.

As apparent from the foregoing, the oriental medicinal composition and the method for preparing the composition according to the present invention prevents hair loss and exhibits superior hair restoration effects.

Since the oriental medicinal composition of the present invention comprises natural foods as major raw materials, it has no toxicity and side effect to humans. That is, by the action of light energy released from quartzite, the oriental medicinal composition of the present invention promotes the absorption of polysaccharides as nutrients, which activate the division of cells, into hair follicles in the telogen phase for a long period of time, and enhances the bloodstream to allow newborn hair to grow in the form of stiff hair. In addition, inhibition of the formation of active oxygen to remove excessively secreted lipid peroxides due to their antibacterial activity, and inhibition of the formation of lipid peroxides to allow hair to be effectively revitalized both occur due to the presence of trisulfide extracted from onion; vitamin C, vitamin B group, and vitamin E (tocopherol) extracted from black bean, oyster mushroom, and ginkgo nut; polysaccharides (e.g., glucose, maltose and tannin) contained as nutrients in taro, potato, and barley; and terpene extracted from pine needles, ginkgo nut, *Fructus lycii*, *Fructus schizandrae*, and *Fructus rubi*

Furthermore, the method for the preparation of the oriental medicinal composition according to the present invention comprises the steps of purifying crude materials, extracting the purified crude materials, concentrating the extracts, filtering the concentrates, drying the filtrates, pulverizing to obtain powders on a nanometer scale, mixing the powders, heating the mixture to dissolve the mixture, and reconcentrating the solution. Accordingly, since the crude drugs are highly water-soluble without the addition of any additive, such as a dispersion auxiliary, the oriental medicinal composition can be uniformly dispersed in a relatively simple manner without the formation of any precipitate.

The invention is further described by the following numbered paragraphs:

1. A natural oriental medicinal composition for the promotion of hair growth, wherein the composition is comprised of a quartzite powder, black bean extract, a tangerine extract, a potato extract, and a pine needle extract.

2. The composition according to paragraph 1, wherein the composition comprises about 100 parts by weight of the quartzite, about 20 to about 200 parts by weight of the black bean extract, about 20 to about 200 parts by weight of the tangerine extract, about 20 to about 200 parts by weight of the potato extract, and about 20 to about 200 parts by weight of the pine needle extract.

3. The composition according to paragraph 1 or 2, further comprising an extract selected from the group consisting of an onion extract, a ginkgo nut extract, a *Fructus schizandrae* extract, a *Fructus lycii* extract, an oyster mushroom extract, and a barley extract.

4. The composition according to paragraph 3, wherein the composition comprises about 50 to about 250 parts by weight of the onion extract, about 30 to about 200 parts by weight of the ginkgo nut extract, about 30 to about 200 parts by weight of the *Fructus schizandrae* extract, about 50 to about 250 parts by weight of the *Fructus lycii* extract, about 30 to about 200 parts by weight of the oyster mushroom extract, and about 20 to about 200 parts by weight of the barley extract, based on about 100 parts by weight of the quartzite.

5. The composition according to paragraphs 1-4, further comprising an extract selected from the group consisting of a taro extract, a *Fructus rubi* extract, a jade powder, a wild ginseng extract, and a loess powder.

6. The composition according to paragraph 5, wherein the composition comprises about 10 to about 150 parts by weight of the taro extract, about 50 to about 250 parts by weight of the *Fructus rubi* extract, about 50 to about 250 parts by weight of the jade powder, about 50 to about 250 parts by weight of the wild ginseng extract and about 50 to about 250 parts by weight of the loess powder, based on about 100 parts by weight of the quartzite.

7. The composition according to paragraphs 1-6, further comprising 1 to 10 parts by weight of a gold powder, based on about 100 parts by weight of the quartzite.

8. A method for preparing an oriental medicinal composition, the method comprising the steps of:
   (i) preparing plant crude drugs from black beans, tangerines, potatoes and pine needles;
   (ii) preparing a mineral crude drug from quartzite;
   (iii) mixing the plant crude drugs with the mineral crude drug; and
   (iv) reconcentrating the mixture by heating.

9. The method according to paragraph 8, wherein the step of preparing the plant crude drugs comprises the sub-steps of:
   (i) heating the selected plants at 90 to 130° C. for 8 to 15 hours and filtering the heated plants to obtain respective extracts from the plants;
   (ii) heating the extracts at 50 to 80° C. for 12 to 48 hours to obtain respective concentrates; and
   (iii) drying the concentrates and pulverizing to obtain respective powders.

10. The method according to paragraph 8 or 9, wherein the reconcentration step is carried out by mixing about 50 to about 250 parts by weight of the mixture of the crude drugs with 100 parts by weight of water and heating the resulting mixture at 80 to 140° C. for 12 to 48 hours.

11. The method according to any one of paragraphs 8-10, wherein the plant crude drugs further include crude drugs obtained from the group consisting of onions, ginkgo nuts, *Fructus schizandrae, Fructus lycii*, oyster mushrooms and barley.

12. The method according to paragraph 11, wherein the plant crude drugs further include crude drugs obtained from the group consisting of taro, *Fructus rubi* and wild ginseng; and the mineral crude drug further includes crude drugs obtained from the group consisting of jade and loess.

13. The method according to paragraph 12, wherein the mineral crude drug further includes a crude drug obtained from gold.

14. A method for preparing an oriental medicinal composition, the method comprising the steps of:
   (i) preparing plant extracts from black beans, tangerines, potatoes and pine needles;
   (ii) preparing mineral powder from quartzite;
   (iii) mixing the plant extracts with the mineral powder; and
   (iv) reconcentrating the mixture by heating.

15. The method according to paragraph 14, wherein the step of preparing the plant extracts comprises the sub-steps of:
   (i) heating the selected plants at 90 to 130° C. for 8 to 15 hours and filtering the heated plants to obtain respective extracts from the plants;
   (ii) heating the extracts at 50 to 80° C. for 12 to 48 hours to obtain respective concentrates; and
   (iii) drying the concentrates and pulverizing to obtain respective powders.

16. The method according to paragraph 14 or 15, wherein the reconcentration step is carried out by mixing about 50 to about 250 parts by weight of the mixture of the plant extracts and mineral powder with about 100 parts by weight of water and heating the resulting mixture at 80 to 140° C. for 12 to 48 hours.

17. The method according to any one of paragraphs 14-16, wherein the plant extracts further include plant extracts obtained from the group consisting of onions, ginkgo nuts, *Fructus schizandrae, Fructus lycii*, oyster mushrooms and barley.

18. The method according to paragraph 17, wherein the plant extracts further include plant extracts obtained from the group consisting of taro, *Fructus rubi* and wild ginseng; and the mineral powder further includes mineral powder obtained from the group consisting of jade and loess.

19. The method according to paragraph 18, wherein the mineral powder further includes a powder obtained from gold.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A composition for promotion of hair growth, comprising:
   100 parts by weight of quartzite;
   20 to 200 parts by weight of a black bean extract;
   20 to 200 parts by weight of a tangerine extract;
   20 to 200 parts by weight of a potato extract;
   20 to 200 parts by weight of a pine needle extract;
   50 to 250 parts by weight of an onion extract;
   30 to 200 parts by weight of a ginkgo nut extract;
   30 to 200 parts by weight of a *Fructus schizandrae* extract;
   50 to 250 parts by weight of a *Fructus lycii* extract;
   30 to 200 parts by weight of an oyster mushroom extract; and
   20 to 200 parts by weight of a barley extract, the plant extracts being prepared by hot-water extraction, concentration, drying and powdering into a mean particle size of 100 μm or smaller, the quartzite being prepared by powdering into a mean size of 100 μm or smaller.

2. The composition according to claim 1, further comprising an extract or powder selected from the group consisting of a taro extract, a Fructus rubi extract, a jade powder, a wild ginseng extract, and a loess powder.

3. The composition according to claim 1, wherein the composition further comprises about 10 to about 150 parts by weight of the taro extract, about 50 to about 250parts by weight of the Fructus rubi extract, about 50 to about 250 parts by weight of the jade powder, about 50 to about 250 parts by weight of the wild ginseng extract and about 50 to about 250 parts by weight of the loess powder.

4. The composition according to claim 1, further comprising about 1 to about 10 parts by weight of a gold powder.

* * * * *